United States Patent [19]

Quadranti et al.

[11] 4,309,210
[45] Jan. 5, 1982

[54] PREEMERGENCE METHOD OF SELECTIVELY CONTROLLING WEEDS IN CROPS OF CEREALS AND COMPOSITION THEREFOR

[75] Inventors: Marco Quadranti, Brugg; Hans-Rudolf Gerber, Pratteln, both of Switzerland

[73] Assignee: Ciba-Geigy Corporation, Ardsley, N.Y.

[21] Appl. No.: 97,027

[22] Filed: Nov. 21, 1979

[30] Foreign Application Priority Data

Dec. 1, 1978 [CH] Switzerland .................. 12305/78

[51] Int. Cl.³ .................. A01N 43/68; A01N 43/40
[52] U.S. Cl. .................. 71/93; 71/88; 71/90; 71/94; 71/95; 71/97; 71/98; 71/100; 71/103; 71/105; 71/106; 71/108; 71/109; 71/111; 71/118; 71/120; 71/124
[58] Field of Search .................. 71/94, 93

[56] References Cited

U.S. PATENT DOCUMENTS

| | | | |
|---|---|---|---|
| 3,492,110 | 1/1970 | Hood et al. | 71/93 |
| 4,021,228 | 5/1977 | Arneklev et al. | 71/93 |
| 4,233,060 | 11/1980 | Böhner et al. | 71/94 |

FOREIGN PATENT DOCUMENTS

| | | | |
|---|---|---|---|
| 483 | 6/1978 | European Pat. Off. | 71/94 |
| 2204 | 11/1978 | European Pat. Off. | 71/94 |
| 43-118 | 1/1968 | Japan | 71/93 |
| 50-42047 | 4/1975 | Japan | 71/93 |

*Primary Examiner*—Glennon H. Hollrah
*Attorney, Agent, or Firm*—Frederick H. Rabin

[57] ABSTRACT

The present invention relates to a preemergence method of selectively controlling weeds in crops of cereals, and to a composition therefor.

Up to now it has been virtually impossible to use s-triazines, phenylureas and other photosynthesis inhibitors as preemergence herbicides in cereals, especially wheat and barley, because of their too potent action. This invention solves the problem by providing a composition for the preemergence control of weeds which, in addition to containing such photosensitive inhibitors, contains a diphenyl ether or pyridylphenyl ether derivative as antagonistic component which neutralizes or greatly diminishes the harmful action in cereals.

In particular, the admixture of known nuclear-substituted phenoxyphenoxyalkanoic acid derivatives or pyridyl-(2)-oxy-phenoxyalkanoic acid derivatives to commercially available 4,6-bis-alkylamino-s-triazines and phenylureas can influence the herbicidal action of these latter so advantageously that, in preemergence application, they no longer damage cereals when employed in conventional concentrations, without losing their potent action against weeds.

5 Claims, No Drawings

PREEMERGENCE METHOD OF SELECTIVELY CONTROLLING WEEDS IN CROPS OF CEREALS AND COMPOSITION THEREFOR

Since their introduction in maize growing, attempts have been made to employ s-triazines, especially chloro-s-triazines, for weed control in cereals cultivation. Under specific climatic and soil conditions it has proved possible to use Simazine (2-chloro-4,6-bis-ethylamino-s-triazine) in concentrations of 200–400 g/ha in preemergence application. However, despite observance of all factors (soil, climate etc.) the cereals were very often damaged. In addition, the low concentration of triazine that does not damage the cereals only sufficed to control a few very susceptible weed species.

From the series of the phenylureas, attempts have also been made to employ Diuron ([N-(3,4-dichlorophenyl)-N'-dimethylurea])—which is still used at the present time in cotton and in fruit growing and viticulture—as selective preemergence herbicide in cereals. In spite of occasional good random results when used as preemergence herbicides in cereals, it has also not been possible to use satisfactorily other phenylureas, such as Fluometuron and Chlorobromuron.

The following significant problems arise in cereals cultivation at the present time. In winter barley, the greatly increased use of chemical fertilisers increasingly gives rise to problems with dicotyledonous weeds. A number of hitherto commonly employed preemergence herbicides are no longer able to cope with this situation. Dense populations of *Viola tricolor, Stellaria media, Veronica* ssp., *Galium aparine,* Polygonum ssp. and other species spring up and cause severe damage to the cultivated plants. Recently, winter wheat has come to be more or less as severely infested with dicots as winter barley. In particular, severe infestation with *Galium, Veronica, Viola tricolor* and the grasses *Alopecurus myos.* and *Lolium perenne,* constitute a substantial problem. In summer wheat and summer barley it has not been possible up to now to use any selective herbicide in preemergence application. All varieties of these cereals have hitherto reacted too sensitively to preemergence herbicides.

Surprisingly, it has now been found that photosynthesis inhibitors, such as s-triazines, phenylureas, and also triazinones and further compounds, such as thiurones and benzthiazurones, are better tolerated by cereals if they are used in preemergence application together with products of the series of the diphenyl ethers and pyridylphenyl ethers, especially as mixtures. This safening action is particularly conspicuous when using chlorotriazines, such as 2-chloro-4-ethylamino-6-tert-butylamino-s-triazine and Simazine. These triazines and other photosynthesis inhibitors do not lose their good activity against weeds, i.e. barley, wheat and rye can be antagonised selectively such that, in preemergence application, they tolerate in all situations a concentration of these triazines and the other compounds specified above which remains fully effective against the most important weed species. The problems outlined above which are encountered in the different species of cereals can thus be solved in preemergence application. Moreover, an originally non-selective herbicide with a broad activity spectrum is elevated to a selective level in antagonistic manner by the addition of diphenyl ethers and pyridylphenyl ethers.

The method of the present invention of selectively controlling weeds in crops of cereals comprises treating the area under cultivation, before emergence of the cultivated plants, on the one hand with a herbicide belonging to the group of the photosynthesis inhibitors, and, on the other, with an anatagonising diphenyl ether or pyridylphenyl ether derivative which neutralises the harmful action of the herbicide on the cereal without impairing the herbicidal action against the weeds.

The treatment with both active ingredients can be carried out in succession in any order, but is preferably effected simultaneously using a composition which contains both active ingredients in admixture, i.e. the photosynthesis-inhibiting herbicide and the diphenyl ether or pyridyl which acts as safener.

Accordingly, it is also an object of the invention to provide such a composition which, in addition to containing conventional carriers and adjuvants, contains a herbicide belonging to the group of the photosynthesis inhibitors and a safener of the diphenyl ether or pyridylphenyl ether series.

Herbicides belonging to the group of the photosynthesis inhibitors are in particular s-triazines, especially chloro- or bromo-bis(alkylamino)-s-triazines and methylthio- or methoxy-bis(alkylamino)-s-triazines, for example: Simazine, Atrazine, Terbutylazine (2-chloro-4-ethylamino-6-tert-butylamino-s-triazine), 2-chloro-4-isopropylamino-6-(γ-methoxypropylamino)-s-triazine, 2-chloro-4-ethylamino-6-sec-butylamino-s-triazine, Propazine, Norazine (2-chloro-4-methylamino-6-isopropylamino-s-triazine), 2-chloro-4-methylamino-6-tert-butylamino-s-triazine, 2-chloro-4-amino-6-isopropylamino-s-triazine, 2-chloro-4-tert-butylamino-6-cyclopropylamino-s-triazine, cyanazine (Bladex), Atraton, Prometon, 2-methoxy-4-ethylamino-6-tert-butylamino-s-triazine, 2-methoxy-4-ethylamino-6-sec-butylamino-s-triazine (=Sumitol), 2-methoxy-4-ethylamino-6-cyclopentylamino-s-triazine, 2-methoxy-4-cyclopropylamino-6-(1-cyano-1-methyl-ethyl)-amino-s-triazine, Ametryn, Prometryn, Terbutryn, 2-ethylthio-4,6-bis(isopropylamino)-s-triazine (=Dipropetryn), 2-methylthio-4-isopropylamino-6-(γ-methoxypropylamino)-s-triazine, Methoprotryn, 2-methylthio-4-methylamino-6-isopropylamino-s-triazine (=Desmetryn), 2-methylthio-4-ethylamino-6-sec-butylamino-s-triazine, 2-methylthio-4-amino-6-tert-butylamino-s-triazine, 2-bromo-4-isopropylamino-6-cyclopropylamino-s-triazine, 2-bromo-4-ethylamino-6-isopropylamino-s-triazine.

Examples of photosynthesis-inhibiting phenylurea herbicides are: Dicuran (Chlortoluron), Loberan, Maloran, Patoran, Isoproturon, N-(3'-chloro-4'-isopropyl)-phenyl-N'-methyl-N'-methoxyurea, Diuron, Monuron, Fenuron, Linuron, Monolinuron, N-(3'-chloro-4'-isopropyl)phenyl-N',N'-dimethylurea, N-(4'-methylaminosulfonyl)-phenyl-N',N'-dimethylurea, Neburon, Tandex (=Karbutilate), Siduron, Beturon, Benzomarc.

Examples of triazinones are: Sencor (Metribuzin), Tantizon, 3-methylthio-4-amino-6-(1'-methylcyclopropyl)-1,2,4-triazinone-5.

Examples of further photosynthesis inhibitors are: Tribunil (Methabenzthiazuron), Gatnon (Benzthiazuron), Noruron, Spike (Tebuthiuron), N-methyl-N-[5-trifluoromethyl-1,3,4-thiadiazolyl-(2)-]-N'-methylurea, 1-[5-methylsulfonyl-1,3,4-thiadiazolyl-(2)]-3-methyl-5-allyl-2-oxohexahydro-s-triazine, N-[3-trifluoromethyl-1,2,4-thiadiazolyl-(5)]-N-methyl-N'-methoxyurea, N-[5- n-butylsulfonyl)-1,3,4-thiadiazolyl-(2)]-N,N'-dimethylurea.

The diphenyl ether and pyridylphenyl ether derivatives which act as safeners for antagonising the harmful action of these herbicides on cereals, have the general formula I

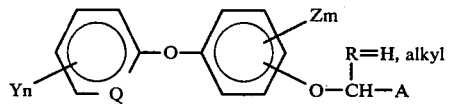

wherein Q is —CH= or —N=; Y and Z are identical or different substituents selected from the group consisting of halogen, alkyl, haloalkyl, such as $CF_3$, nitro, cyano,

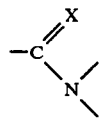

or —X-alkyl, wherein X is oxygen or sulfur; each of n and m is an integer from 0 to 3, and A is —CN, —CO—B, wherein B is —$OR_4$, —$SR_5$,

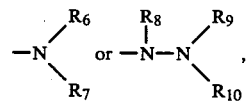

—CS—D, wherein D is

$Q_1$, V, W or hydrogen.

The individual subgroups are as defined as follows:
$R_4$ represents hydrogen or the cation of a base $1/n$ $M^{n\oplus}$, M represents an alkali metal cation or alkaline earth metal cation or an iron, copper, zinc, manganese or nickel cation or an ammonio radical

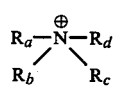

and n is an integer 1, 2 or 3 corresponding to the valency of the cation, while $R_a$, $R_c$ and $R_d$, each independently of the other, represent hydrogen, benzyl or a $C_1$-$C_4$ alkyl or benzyl radical which is unsubstituted or substituted by —OH, —$NH_2$, halogen, CN, nitro, $CF_3$ or $C_1$-$C_4$ alkoxy.

$R_a$ and $R_b$ together with the nitrogen atom to which they are attached also represent a 3- to 7-membered heterocyclic radical.

Further meanings of $R_4$ are:
a $C_1$-$C_{18}$ alkyl radical which is unsubstituted or substituted by halogen, nitro, cyano, $C_1$-$C_{18}$ alkoxy, hydroxyl, $CF_3$, $C_2$-$C_8$ alkoxyalkoxy which in turn can be substituted by halogen, hydroxyl, $CF_3$ or $C_1$-$C_4$ alkoxy; or by $C_3$-$C_6$ alkenyloxy, $C_1$-$C_8$ alkylthio, $C_1$-$C_8$ alkylsulfinyl or $C_1$-$C_8$ alkylsulfonyl, $C_1$-$C_8$ alkylsulfinyloxy or $C_1$-$C_8$ sulfonyloxy, $C_2$-$C_8$ alkanoyl, $C_2$-$C_8$ acyloxy, $C_2$-$C_8$ alkoxycarbonyl, and also by the group

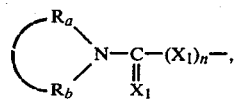

in which $X_1$ is O or S, n is an integer from 0 to 1, and $R_a$ and $R_b$ can also be a $C_2$-$C_6$ alkylene bridge; and furthermore by the group

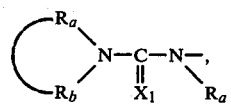

the group

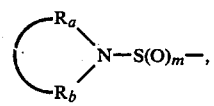

in which
m is an integer from 1 to 2; by the group $C_1$-$C_5$ alkoxy-$S(O)_m$—$(O)_n$—, the amino radical

or the ammonio radical

$C_3$-$C_8$ cycloalkyl, $C_3$-$C_8$ cycloalkenyl, or also by a phenyl, phenoxy or phenyl-$S(O)_m$—$(O)_n$-radical, in which m is 0 to 2 and n is again an integer from 0 to 1, which is unsubstituted or mono- or polysubstituted by halogen, $C_1$-$C_4$ alkyl, $C_1$-$C_4$ alkoxy; a 5- to 6-membered heterocyclic radical containing 1 to 3 heteroatoms;

a $C_3$-$C_{18}$ alkenyl radical which is unsubstituted or mono- or tetrasubstituted by halogen or monosubstituted by phenyl or methoxycarbonyl;

a $C_3$-$C_8$ alkynyl radical which is unsubstituted or substituted by $C_1$-$C_4$ alkoxy, phenyl, halophenyl or $C_1$-$C_4$ alkylphenyl;

a $C_3$-$C_{12}$ cycloalkyl radical which is unsubstituted or substituted by halogen, hydroxyl, $CF_3$, $C_1$-$C_4$ alkoxy or $C_1$-$C_4$ alkyl;

a $C_3$-$C_8$ cycloalkenyl radical;

a phenyl or naphthyl radical which is unsubstituted or mono- or polysubstituted by halogen, $C_1$-$C_4$ alkyl, $C_1$-$C_4$ alkoxy, $C_1$-$C_4$ alkylthio, $NO_2$, $CF_3$, COOH, CN, OH, $SO_3H$, $NH_2$ or —NH($C_1$-$C_4$ alkyl) or —N($C_1$-$C_4$ alkyl)$_2$;

a 5- to 6-membered heterocyclic ring containing 1 to 3 heteroatoms.

$R_5$ is a radical which can be as defined for $R_4$.
$R_6$ is:

hydrogen or a $C_1$–$C_{18}$ alkyl radical which is unsubstituted or substituted by halogen, —CN, —OH, —COOH, $C_2$–$C_5$ alkoxycarbonyl, $C_1$–$C_4$ alkoxy, phenoxy, $C_3$–$C_{12}$ cycloalkyl, a 5- to 6-membered heterocyclic radical containing 1 to 3 heteroatoms, the amino radical

the ammonio radical

or by a phenyl radical which is in turn substituted by halogen, $C_1$–$C_4$ alkyl or $C_1$–$C_4$ alkoxy;
a phenyl radical which is unsubstituted or substituted by halogen, $C_1$–$C_4$ alkyl, $C_1$–$C_4$ alkoxy, $C_1$–$C_4$ alkylthio, $NO_2$, —$CF_3$, —COOH, —CN, —OH, —$SO_3H$, $NH_2$, $NH(C_1$–$C_4)$alkylamino, N,N-bis(-$C_1$–$C_4$ alkyl)amino;
a $C_3$–$C_{12}$ cycloalkyl radical; a $C_3$—$C_{18}$ alkenyl radical; a $C_3$–$C_8$ alkynyl radical.

$R_7$ is:
a hydroxyl group or a $C_1$–$C_5$ alkoxy radical or can have one of the meanings assigned to $R_6$;
a 5- to 6-membered heterocyclic ring system which can contain 1 or 2 additional heteroatoms, or together with $R_1$ and the nitrogen atom to which they are attached is a 3- to 10-membered heterocyclic radical which, depending on the number of members, can consist of 1 or 2 rings containing 1 or 2 additional heteroatoms, and which can be mono- to tetrasubstituted by halogen or $C_1$–$C_4$ alkyl;
a $C_2$–$C_8$ alkanoyl radical; a $C_2$—$C_8$ alkoxycarbonyl radical; a $C_2$–$C_8$ alkanoyl-$(C_1$–$C_4)$alkyl radical;
the group

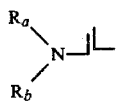

$R_8$ is:
hydrogen or a $C_1$–$C_4$ alkyl radical which is unsubstituted or substituted by —OH, —CN or a $C_1$–$C_4$ alkoxy radical;
a phenyl radical which is unsubstituted or substituted by halogen, $C_1$–$C_4$ alkyl or $C_1$–$C_4$ alkoxy.

$R_9$ is:
a $C_1$–$C_4$ alkyl radical which is unsubstituted or substituted by —OH, —CN or a $C_1$–$C_4$ alkoxy radical;
a phenyl radical which is unsubstituted or substituted by halogen, $C_1$–$C_4$ alkyl or $C_1$–$C_4$ alkoxy;
a $C_2$–$C_8$ alkanoyl radical;
a benzoyl radical.

$R_{10}$ has the same meanings as assigned to $R_9$, whilst $R_9$ and $R_{10}$ together with the nitrogen atom to which they are attached can form a 5- to 6-membered heterocyclic ring system which is unsubstituted or substituted by $C_1$–$C_4$ alkyl, and $R_9$ and $R_{10}$ together with both nitrogen atoms to which they are attached can form a partially or completely hydrogenated pyrazole or pyridazine ring.

$Q_1$ is:

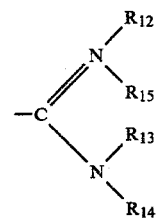

wherein $R_{11}$ is H, $(C_1$–$C_5)$alkyl or —$CH_2$—COOH—, or $$\begin{array}{c} \diagup N-R_{12} \\ -C \diagdown \diagup R_{13} \\ N \\ \diagdown R_{14} \end{array}$$

or the non-phytotoxic salts thereof with inorganic and organic acids, wherein $R_{12}$ has the same meaning as $R_{13}$ and $R_{14}$, with the proviso that only one of the three radicals can be alkoxy or alkylthio and $R_{13}$ is H, $(C_1$–$C_6)$alkyl, $(C_1$–$C_6)$alkoxy, $(C_1$–$C_6)$alkylthio, $(C_5$–$C_6)$cycloalkyl, benzyl or phenyl, which can be mono- to trisubstituted by halogen, $CF_3$, $NO_2$, $C_1$–$C_4$alkyl, $C_1$–$C_4$alkoxy and/or $C_1$–$C_4$alkylthio, and $R_{14}$ is H, $(C_1$–$C_6)$alkyl, $(C_5$–$C_6)$cycloalkyl or benzyl, or $R_{13}$ and $R_{14}$ together form an alkylene chain containing 2 to 5 carbon atoms which can also be interrupted by —O—, —S— or $N(C_1$–$C_4)$alkyl;

$$\begin{array}{c} \diagup R_{12} \\ N \\ \diagup \diagdown R_{15} \\ -C \\ \diagdown \diagup R_{13} \\ N \\ \diagdown R_{14} \end{array}$$

wherein $R_{12}$ and $R_{15}$ have the same meanings as $R_{13}$ and $R_{14}$, with the proviso that only one of the four radicals can be alkoxy or alkylthio and none of these radicals is hydrogen, and $A^-$ is the radical of an inorganic or organic acid;

$$-C\diagup^{N-R_{12}}_{X-R_{16}} \quad \text{or} \quad -C\diagup^{H}_{X-R_{16}}{}^{N-R_{13}},$$

wherein $R_{16}$ is $(C_1$–$C_6)$alkyl, $C_3$–$C_6$alkenyl, $(C_3$–$C_6)$alkynyl, $(C_5$–$C_6)$cycloalkyl, phenyl optionally substituted by halogen, $CF_3$, $NO_2$, $(C_1$–$C_4)$alkyl, $(C_1$–$C_4)$alkoxy or $(C_1$–$C_4)$alkylthio.

$Q_1$ is furthermore $$\begin{array}{c} O \\ \parallel \\ -C-N\diagdown(CR_{17}R_{18})_n \end{array},$$

wherein $R_{17}$ and $R_{18}$ are $C_1$–$C_4$alkyl, H, and n is 2 to 3.

V is:

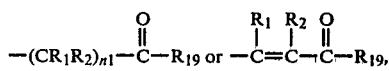

wherein R$_{19}$ is H, OR$_4$, or has the same meaning as R$_{16}$, a C$_1$–C$_5$alkyl radical which is unsubstituted or substituted by C$_2$–C$_5$alkanoyl, unsubstituted or substituted aroyl, C$_1$–C$_5$alkoxycarbonyl, and n$_1$ is an integer from 0 to 5;

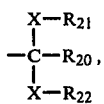

wherein R$_{21}$ and R$_{22}$ are (C$_1$–C$_4$)alkyl or together form an alkylene chain containing 2 to 3 carbon atoms and R$_{20}$ is H or has the same meaning as R$_{16}$;

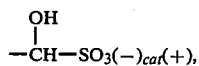

wherein cat$^\oplus$ is the cation of an inorganic or organic base;

—CH=N—W—R$_{20}$ wherein W is a direct bond, —O—, —N(R$_{20}$)—, —O—C(O)—, —O—C(O)—N(R$_{20}$)—, or NH—C—(O-)—N(R$_{20}$).

W is the group

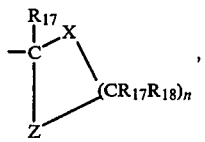

wherein Z has the meaning of X or is

The active ingredients falling under the formula I and acting as safeners are either known or form the subject-matter of pending patent applications. Attention is drawn to the following publications as constituting prior art in which such active ingredients are disclosed:
German Offenlegungsschrift Nos.:
   2 223 894
   2 531 643
   2 546 251
   2 604 282
   2 611 695
   2 613 697
   2 617 804
   2 628 384
   2 639 796
   2 646 124
   2 715 284
   2 730 591
Japanese published patent specifications Nos.:
   1 142 537
   2 131 542

British Pat. No. 1,224,723

The following list of compounds constitutes a selection of derivatives of the formula I which are suitable for use as safeners:

1. 2-(4'-bromophenoxy)-4,5-dibromo-α-phenoxypropionic acid methyl ester (oil)
2. 2-(4'-chlorophenoxy)-4,5-dibromo-α-phenoxypropionic acid (mp. 124°–127° C.)
3. 4-(5'-chloropyridyl-2'-oxy)-α-phenoxypropionic acid (mp. 86°–88° C.)
4. 2-(2',4'-dichlorophenoxy)-5-chlorophenoxyacetic acid ethyl ester (m.p. 52°–54° C.)
5. 4-(4'-aminocarbonylphenoxy)-α-phenoxypropionic acid (m.p. 184°–185° C.)
6. 4-(3'-methyl-4'-nitrophenoxy)-α-phenoxypropionic acid methyl ester (b.p. 190°–217° C./0.5 torr)
7. 3-(2'-trifluoromethylphenoxy)-α-phenoxypropionic acid methyl ester (b.p. 140°–145° C./0.5 torr)
8. 4-(2'-chloro-4'-trifluoromethylphenoxy)-3-bromo-α-phenoxypropionic acid methyl ester (b.p. 175° C./0.35 torr)
9. 4-(2'-cyano-4'-trifluoromethylphenoxy)-α-phenoxypropionic acid phenyl ester (m.p. 97°–99° C.)
10. 4-(2'-cyano-4'-chlorophenoxy)-α-phenoxypropionic acid isopentyl ester (n$_D^{37}$=1.5470)
11. 4-(2'-chloro-4'-cyanophenoxy)-α-phenoxypropionic acid sec-butyl ester (n$_D^{37}$=1.5514)
12. 4-(2'-chloro-4'-cyanophenoxy)-α-phenoxypropionic acid (2'-methylbutyl) ester (n$_D^{39}$=1.5500)
13. 4-(2'-chloro-4'-cyanophenoxy)-α-propionic acid (2'-methylpentyl) ester (n$_D^{40}$=1.5422)
14. 4-(3',5'-dichloropyridyl-2'-oxy)-α-phenoxypropionic acid methyl ester (m.p. 82°–84° C.)
15. 4-(4'-trifluoromethylphenoxy)-α-phenoxy-thiopropionic acid methallyl ester (n$_D^{22}$=1.5403)
16. 4-(4'-trifluoromethylphenoxy)-α-phenoxy-thiopropionic acid (buten-(2)-yl) ester (n$_D^{22}$=1.5455)
17. 4-(4'-trifluoromethylphenoxy)-α-phenoxypropionic (ethoxycarbonylmethyl) amide (m.p. 65°–67° C.)
18. 4-(4'-trifluoromethylphenoxy)-α-phenoxypropionic acid propargyl ester (m.p. 55°–57° C.)
19. 4-(4'-chlorophenoxy)-α-phenoxy-thiopropionic acid n-propyl ester (n$_D^{22}$=1.5717)
20. 4-(4'-trifluoromethylphenoxy)-α-phenoxy-thiopropionic acid (4'-chlorobutin-(2)-yl) ester (n$_D^{22}$=1.5505)
21. 4-(4'-trifluoromethylphenoxy)-α-phenoxy-thiopropionic acid cyanomethyl ester (n$_D^{22}$=1.5417)
22. 4-(4'-trifluoromethylphenoxy)-α-phenoxy-thiopropionic acid (2'-chloroethyl) ester (n$_D^{22}$=1.5390)
23.

$$CF_3-\!\!\bigcirc\!\!-O-\!\!\bigcirc\!\!-O-\overset{CH_3}{\underset{|}{CH}}-(CH_2)_2-COOC_2H_5$$

(n$_D^{21}$=1.5009)

24.

$$CF_3-\!\!\bigcirc\!\!-O-\!\!\bigcirc\!\!-O-\overset{CH_3}{\underset{|}{CH}}-CH=CH-COOC_2H_5$$

(n$_D^{21}$=1.5128)

25. pyridinium salt of 4-(trifluoromethylphenoxy)-α-phenoxy-thiopropionic acid (m.p. 82°–83° C.)

26. 4-(4'-trifluoromethylphenoxy)-α-phenoxy-thiopropionic acid (2'-bromoallyl) ester ($n_D^{22}=1.5502$)
27. 4-(4'-trifluoromethylphenoxy)-α-phenoxypropionitrile ($n_D^{22}=1.5086$)
28. 4-(4'-trifluoromethylphenoxy)-α-phenoxypropionic acid cyanamide (m.p. 95°–97° C.)
29. 4-(5'-trifluoromethyl-6'-chloropyridyl-2'-oxy)-α-phenoxypropionic acid methyl ester (m.p. 72°–76° C.)
30.

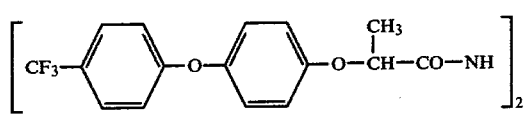

(m.p. 167°–168° C.)

31.

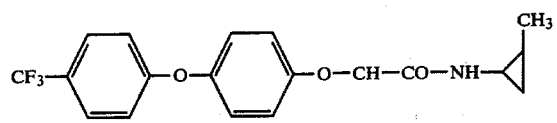

(m.p. 107°–109° C.)

32.

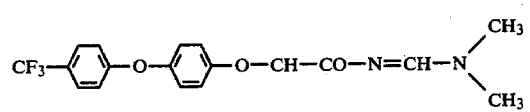

($n_D^{21}=1.5264$)

33. N,N-dimethyl-cyclohexylammonio salt of 4-(4'-trifluoromethylphenoxy)-α-phenoxy-thiopropionic acid (m.p. 114°–116° C.)

34.

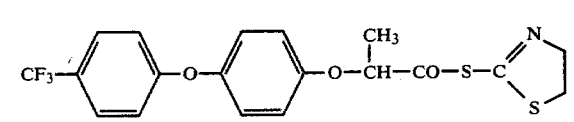

35.

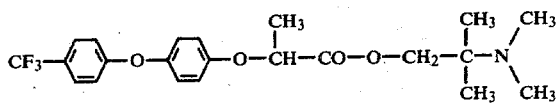

($n_D^{21}=1.5049$)

36.

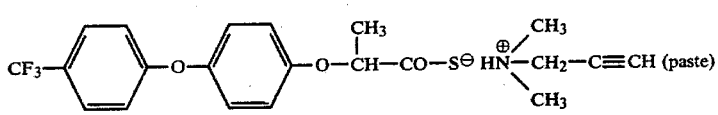

(paste)

37.

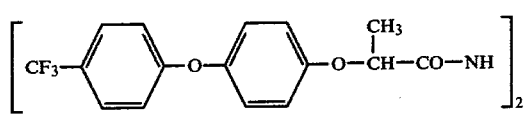

($n_D^{21}=1.5223$)

38.

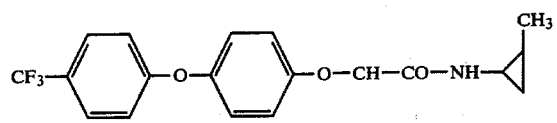

(m.p. 110°–117° C.)

39.

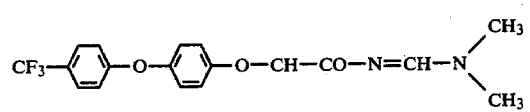

($n_D^{22}=1.5183$)

40.

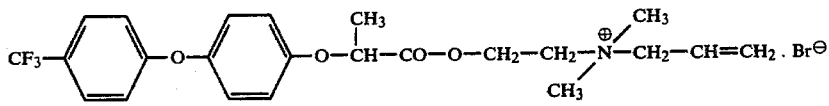

(m.p. 112°–114° C.)

41.

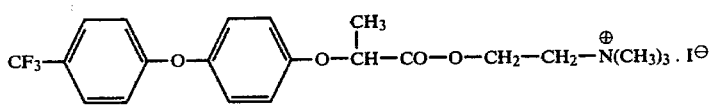

(m.p. 58°–60° C.)

42.

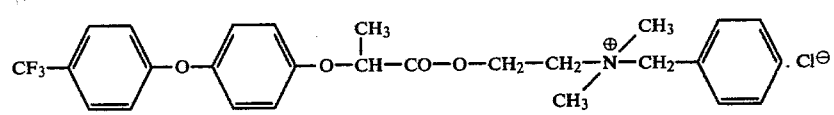

(m.p. 110°–112° C.)

43. 4-(4'-chloro-5'-trifluoromethylpyridyl-(2')-oxy)-α-phenoxypropionic acid methyl ester ($n_D^{30}=1.5200$)
44. 4-(3',5'-dichloropyridyl-(2')-oxy)-α-phenoxy-thiopropionic acid (m.p. 85°–87° C.)
45. 4-(3',5'-dichloropyridyl-2'-oxy)-α-phenoxy-thiopropionic acid allyl ester ($n_D^{21}=1.5854$)
46. N,N-dimethylcyclohexylammonio salt of the acid (44) ($n_D^{21}=1.5881$)
47. 4-(3',5'-dichloropyridyl-2'-oxy)-α-phenoxypropionamide (m.p. 173°–175° C.)
48. 4-(3',5'-dichloropyridyl-2'-oxy)-α-phenoxypropionic acid (2'-dimethylaminoethyl) ester ($n_D^{20}=1.5498$)
49. 4-(3',5'-dichloropyridyl-2'-oxy)-α-phenoxy-thiopropionic acid β-chloroethyl ester ($n_D^{20}=1.5872$)
50. 4-(3',5'-dichloropyridyl-2'-oxy)-α-phenoxy-thiopropionic acid cyanomethyl ester (m.p. 85°–88° C.)
51. 4-(3',5'-dichloropyridyl-2'-oxy)-α-phenoxy-thiopropionic acid propargyl ester ($n_D^{21}=1.5988$)
52. 4-(3',5'-dichloropyridyl-2'-oxy)-α-phenoxy-thiopropionic acid methyl ester ($n_D^{21}=1.5796$)
53. 4-(3',5'-dichloropyridyl-2'-oxy)-α-phenoxy-thiopropionic acid β-diethylaminoethyl ester ($n_D^{20}=1.5616$)
54.

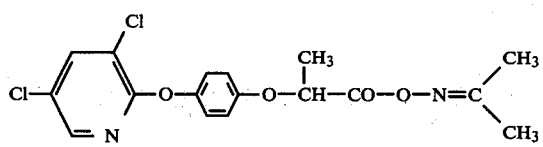

($n_D^{20}=1.5678$)

55. 4-(3',5'-dichloropyridyl-2'-oxy)-α-phenoxy-thiopropionic acid phenyl ester ($n_D^{20}=1.6169$)
56. 4-(2',4'-dichlorophenoxy)-phenylisopropyl ether ($n_D^{20}=1.5676$)
57.

($n_D^{20}=1.5420$)
58.

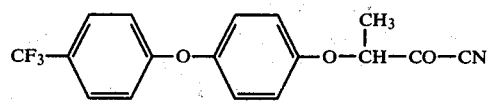

($n_D^{20}=1.5240$)
59.

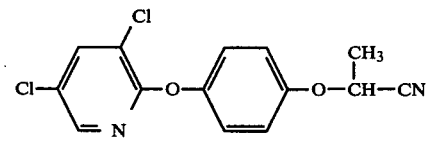

(m.p. 97°–98° C.)
60. 4-(3',5'-dichloropyridyl-2'-oxy)-α-phenoxypropionic acid β-hydroxyethylamide (m.p. 77°–80° C.)
61. di-(β-hydroxyethyl)ammonio salt of 4-(3',5'-dichloropyridyl-2'-oxy)-α-phenoxypropionic acid (m.p. 88°–91° C.)
62. 4-(3',5'-dichloropyridyl)-2'-oxy)-α-phenoxypropionic acid isopropyl ester ($n_D^{20}=1.5357$)
63. 4-(3',5'-dichloropyridyl-2'-oxy)-α-phenoxypropionic acid carboxymethylamide (m.p. 111°–114° C.)
64. 4-(4'-trifluoromethylphenoxy)-α-phenoxypropionic acid 2'-chlorocyclohexyl ester ($n_D^{20}=1.5152$)
65. 4-(3',5'-dichloropyridyl)-2'-oxy)-α-phenoxypropionic acid 2'-chlorocyclohexyl ester ($n_D^{20}=1.5381$)
66. 4-(4'-trifluoromethylphenoxy)-α-phenoxypropionic acid (2'-methyl-4',6'-dinitrophenyl) ester (oil)
67. 4-(3',5'-dichloropyridyl-2'-oxy)-2-chloro-α-phenoxypropionic acid ethyl ester ($n_D^{20}=1.5613$)
68. 4-(3',5'-dichloropyridyl-2'-oxy)-2-chloro-α-phenoxypropionic acid (m.p. 136°–140° C.)
69.

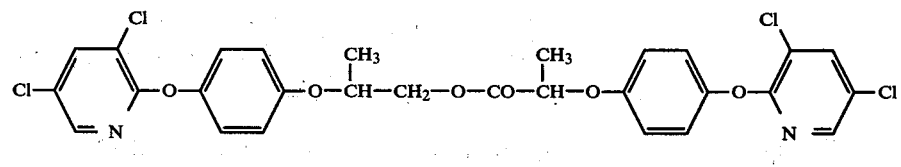

($n_D^{20}=1.5802$)
70.

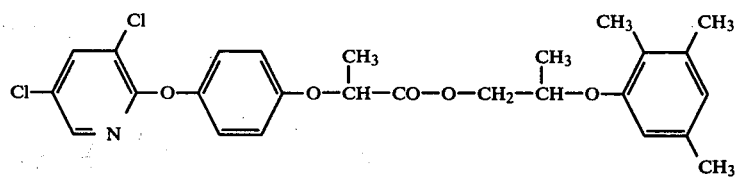

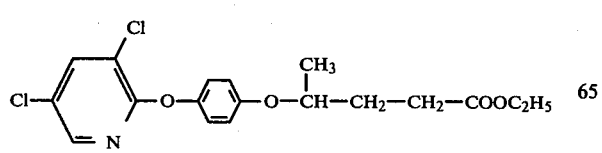

($n_D^{20}=1.5503$)
71.

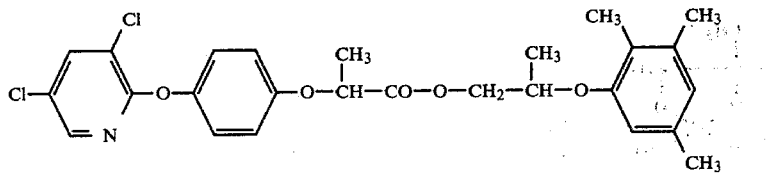

($n_D^{20}$=1.5486)

72. 4-(3',5'-dichloropyridyl-2'-oxy)-chloro-α-phenoxy-thiopropionic acid (m.p. 63°–66° C.)
73. The allyl ester of the acid (72), ($n_D^{20}$=1.5888)
74. 4-(3',5'-dichloropyridyl-2'-oxy)-α-phenoxypropionic acid methyl ester;
   (a) α-isomer:
      m.p. 75° C.
      $[\alpha]_D$=+31° C.
   (b) l-isomer:
      m.p. 75° C.
      $[\alpha]_D$=−32° C.
75.

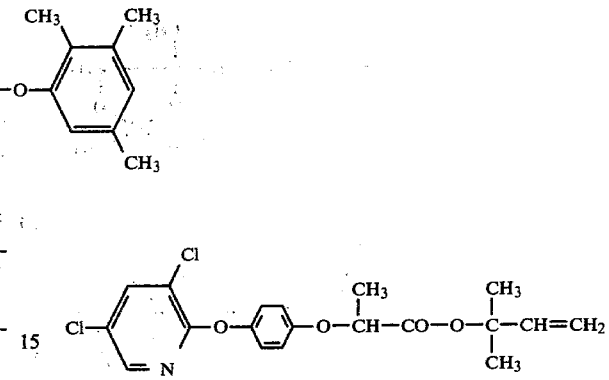

($n_D^{25}$=1.5456)

80.

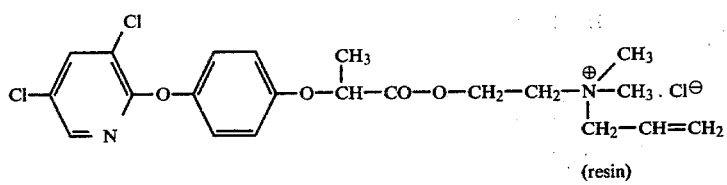

76.

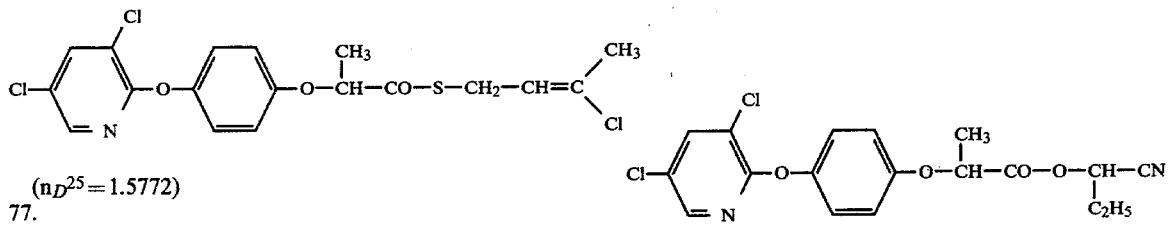

77.

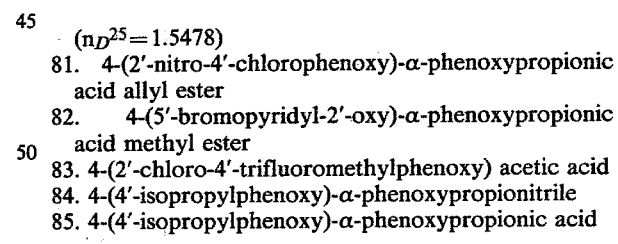

($n_D^{25}$=1.5772)

($n_D^{25}$=1.5478)

81. 4-(2'-nitro-4'-chlorophenoxy)-α-phenoxypropionic acid allyl ester
82. 4-(5'-bromopyridyl-2'-oxy)-α-phenoxypropionic acid methyl ester
83. 4-(2'-chloro-4'-trifluoromethylphenoxy) acetic acid
84. 4-(4'-isopropylphenoxy)-α-phenoxypropionitrile
85. 4-(4'-isopropylphenoxy)-α-phenoxypropionic acid

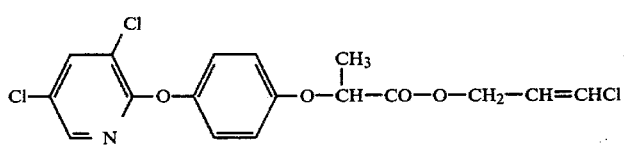

($n_D^{25}$=1.5667)

78.

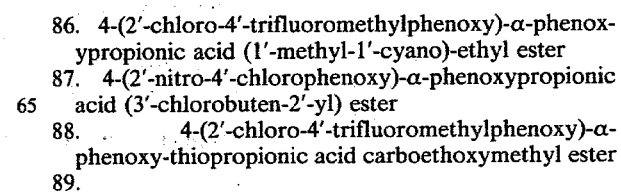

86. 4-(2'-chloro-4'-trifluoromethylphenoxy)-α-phenoxypropionic acid (1'-methyl-1'-cyano)-ethyl ester
87. 4-(2'-nitro-4'-chlorophenoxy)-α-phenoxypropionic acid (3'-chlorobuten-2'-yl) ester
88. 4-(2'-chloro-4'-trifluoromethylphenoxy)-α-phenoxy-thiopropionic acid carboethoxymethyl ester ($n_D^{25}$=1.553)

79.

89.

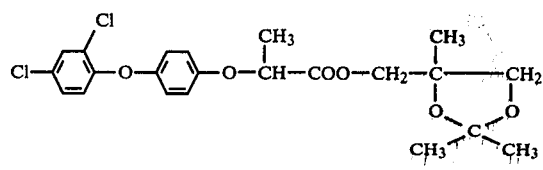

90.

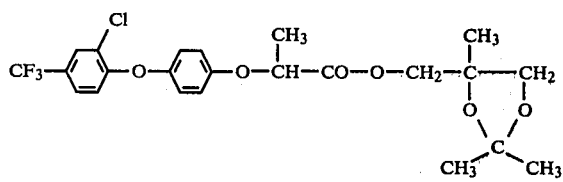

91. 4-(2'-diallylamino-4'-chlorophenoxy)-α-phenoxypropionic acid methyl ester
92.

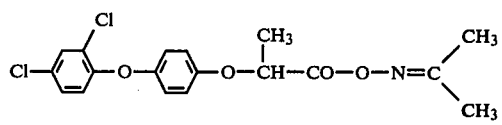

93.

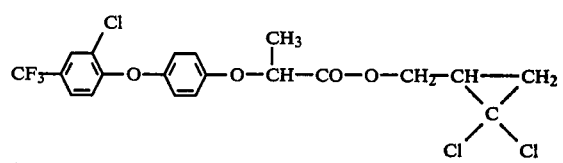

94. 4-(2'-chloro-4'-trifluoromethylphenoxy)-α-phenoxypropionic acid diethyl amide
95.

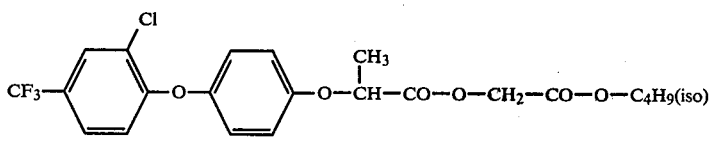

96. 4-(2'-dimethylamino-4'-trifluoromethylphenoxy)-α-phenoxypropionic acid methyl ester
97. 4-(2',4'-dichlorophenoxy)-α-phenoxypropionic acid n-butoxyethyl ester (oil)
98. 4-(2',4'-dichlorophenoxy)-α-phenoxy)-propionic acid (3'-methoxypropyl-2') ester (oil)
99. 4-(2'-nitro-4'-chlorophenoxy)-α-phenoxypropionic acid (2,6-dichlorobenzyl) ester (oil)
100. 4-(2'-nitro-4'-chlorophenoxy)-α-phenoxypropionic acid (2,4-dichlorobenzyl) ester (oil)
101. 3-(2'-chloro-4'-trifluoromethylphenoxy)-α-phenoxy-thiopropionic acid methyl ester (b.p. 145°–50° C./0.05 torr)
102. 4-(4'-cyanophenoxy)-α-phenoxypropionic acid n-propyl ester (oil)
103.

104. 4-(2'-cyano-4'-chlorophenoxy)-α-phenoxypropionic acid allyl amide (m.p. 134°–6° C.)
105. 4-(2',5'-dichlorophenoxy)-α-phenoxypropionic acid methyl ester (oil)

It is particularly surprising that many of the compounds of the formula I listed above, if used alone, themselves possess herbicidal properties, but when used together with herbicides belonging to the series of the photosynthesis inhibitors (triazines, phenylureas etc.) act as antidotes and antagonise the harmful action of these photosynthesis inhibitors on cereals as safeners, but without neutralising or noticeably diminishing the herbicidal action against weeds.

The herbicidal photosynthesis inhibitors and the antagonists of the formula I are used in preemergence application in cereals (wheat, rye, barley, oats), and, if desired, also in maize and rice.

Application can be made simultaneously or in succession in any order, but preferably simultaneously, using a composition which contains both components. The preferred concentration is in the range between 0.5 and 2 kg/ha of photosynthesis inhibitor and about equal amounts of antagonist of the formula I.

The ratio of photosynthesis inhibitor to antagonist can vary between 4:1 and 1:4, but is preferably in the region of 1:1 or of a slight excess of photosynthesis inhibitor.

The preemergence application of the composition is preferably made after sowing from a tank mixture of the composition. However, it is also possible to treat the furrows before sowing. A pretreatment of the seeds (seed dressing) with certain active ingredient combinations is also possible.

Among the photosynthesis inhibitors, extensive preemergence tests were carried out with 2-chloro-4-ethylamino-6-tert-butylamino-s-triazine ("Terbutylazine") of the formula

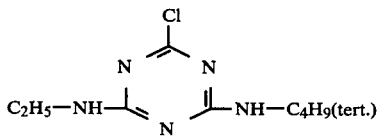

with excellent results in respect of neutralising the phytotoxicity in different cereals in joint application with a very wide range of antagonists of the formula I.

However, good results were also obtained with other triazines, such as Terbutryn, Prometryn, 2-methoxyethylamino-6-tert-butylamino-s-triazine, 2-methoxy-4-ethylamino-6-sec-butylamino-s-triazine, Simazine, Atrazine, 2-chloro-4-isopropylamino-6-(γ-methoxypropylamino)-s-triazine, 2-ethylthio-4,6-bis (isopropylamino)-s-triazine ("Cotofor").

Although most experiments have been carried out up to now with triazines, good results have also been obtained with phenylureas, such as Monuron and Dicuran (chlortoluron).

Test results obtained by preemergence application of mixtures of triazines and antagonists of the formula I in cereals and weeds are reported below in order to demonstrate the reduced phytotoxicity of the composition of the invention in cereals while retaining the herbicidal action against weeds:

PREEMERGENCE ANTIDOTE TEST (Basic Test)

General test method

In a greenhouse, small flavor pots or beakers (diameter at the top 6 cm or 11 cm) are filled with normal soil into which the respective cultivated plant and weed are sown. The soil is then gently pressed firm. A liquid formulation of a mixture of antidote and triazine or phenylurea herbicide in a specific mixture ratio is sprayed onto the flower pots in amounts corresponding to specific concentrations in kg/ha of active ingredient. One group of flower pots is treated only with herbicidal spray mixtures without antidote for control purposes. After the pots have stood for 3 weeks at 20°–23° C. and 60–70% relative humidity, the test is evaluated in accordance with a linear rating from 1 to 9 as follows:

1 = plant completely withered
9 = plants undamaged (as untreated controls) and
2–8 = intermediate stages of damage
5 = 50% action Test 1

(a) herbicide (H): 2-chloro-4-ethylamino-6-tert-butylamino-s-triazine: 1 and 2 kg/ha
(b) mixture of H with antidote (A) No. 53 [4-(3',5'-dichloropyridyl)-2'-oxy)-α-phenoxy-thiopropionic acid β-diethylaminoethyl ester] in the ratios (concentrations) of H:A = 2:4, 2:2 and 1:2 kg/ha.

Test plants: wheat, "Farnese" variety

| Alopecurus myosuroides |        |
|---|---|
| Avena fatua | weeds. |
| Stellaria media | |
| Viola tricolor | |

Results:

| test plants Products | | Wheat | | Alopecurus | | Avena fatua | | Stellaria media | | Viola tricolor | |
|---|---|---|---|---|---|---|---|---|---|---|---|
| H | A | H alone | H + A | H | H + A | H | H + A | H | H + A | H | H + A |
| kg/ha | | | | | | | | | | | |
| 2 | 4 | 1 | 7 | 1 | 1 | 1 | 2 | 1 | 1 | 1 | 1 |
| 2 | 2 | 1 | 8 | 1 | 1 | 1 | 2 | 1 | 1 | 1 | 1 |
| 1 | 2 | 2 | 8 | 1 | 1 | 1 | 2 | 1 | 1 | 1 | 1 |

The three different mixtures H+A leave the wheat virtually undamaged, whereas the herbicide H alone destroys the wheat completely. No differences in the total damage to the weeds are recorded, regardless of whether the herbicide is used alone or in admixture with the antidote No. 53.

Test 2

Determination of the phytotoxicity of 2-chloro-4-ethylamino-6-tert-butylamino-s-triazine (H) in admixture with other antidotes of the formula I to wheat of the Farnese variety.

Concentration (a):
herbicide (H): 1.5 kg/ha (0.15 g/m²)
antidote (A): 4.0 kg/ha (0.4 g/m²)
(see No. of the antidote table)

Concentration (b):
herbicide (H): 1 or 2 kg/ha
antidote (A): 4.2 or 1 kg/ha

The use of 1 kg/ha of herbicide alone resulted in a damage rating of 3. The damage rating was 2 on using 2 kg/ha of herbicide alone. The damage rating was 3 on using 1.5 kg/ha of herbicide alone.

| (a) | A No. | Rating herbicide (H) (1.5 kg/ha) + antidote (A) (4.0 kg/ha) |
|---|---|---|
| | 10 | 6 |
| | 11 | 7 |
| | 13 | 7 |
| | 15 | 8 |
| | 16 | 8 |
| | 19 | 8 |
| | 20 | 7 |
| | 26 | 9 |
| | 27 | 8 |
| | 33 | 7 |
| | 35 | 7 |
| | 42 | 6 |
| | 44 | 8 |
| | 45 | 7 |
| | 46 | 6 |
| | 47 | 8 |
| | 48 | 7 |
| | 49 | 7 |
| | 50 | 7 |
| | 51 | 8 |
| | 53 | 8 |
| | 54 | 7 |
| | 55 | 7 |

| | | H + A | | | |
|---|---|---|---|---|---|
| (b) | A No. | 2 + 4 kg/ha | 2 + 4 kg/ha | 1 + 2 kg/ha | 1 + 1 kg/ha |
| | 10 | 4 | 4 | 7 | 4 |
| | 11 | 2 | 3 | 6 | 8 |
| | 13 | 3 | 3 | 7 | 8 |
| | 15 | 6 | 6 | 8 | 8 |
| | 16 | 7 | 7 | 7 | 8 |
| | 19 | 3 | 3 | 6 | 6 |
| | 20 | 3 | 8 | 8 | 8 |
| | 26 | 7 | 7 | 8 | 8 |
| | 27 | 5 | 7 | 8 | 8 |
| | 33 | 5 | 7 | 9 | 9 |
| | 35 | 4 | 8 | 9 | 8 |
| | 42 | 4 | 5 | 8 | 9 |

-continued

| A (b) No. | H + A 2 + 4 kg/ha | 2 + 4 kg/ha | 1 + 2 kg/ha | 1 + 1 kg/ha |
|---|---|---|---|---|
| 44 | 7 | 6 | 8 | 8 |
| 45 | 8 | 7 | 9 | 8 |
| 46 | 4 | 3 | 8 | 9 |
| 47 | 7 | 8 | 9 | 9 |
| 48 | 6 | 8 | 9 | 9 |
| 49 | 5 | 5 | 9 | 8 |
| 50 | 3 | 4 | 8 | 8 |
| 51 | 7 | 7 | 8 | 9 |
| 53 | 7 | 8 | 8 | 9 |
| 54 | 6 | 8 | 9 | 9 |
| 55 | 6 | 8 | 9 | 9 |

Remarks on (b): Whereas in a few cases the addition of some antidotes achieves no satisfactory reduction of phytotoxicity at the higher herbicide concentration of 2 kg/ha, the improvements in the phytotoxicity values on the addition of antidote to 1 kg/ha of herbicide are strikingly good for *all* antidotes employed in the test. It was possible to confirm the results reported in the table for antidote No. 51[4-(3',5'-dichloropyridyl-2'-oxy)-phenoxy-thiopropionic acid propargyl ester] in 3 small field tests carried out in the Basel area.

Test 3

Determination of the reduction in phytotoxicity of a number of triazines and phenylureas in admixture with a number of selected antidotes in summer wheat and summer barley.

Herbicides:
  I. Igran = Terbutryn
  II. Prometryn
  III. 2-methoxy-4-ethylamino-6-tert-butylamino-s-triazine
  IV. Simazine
  V. Atrazine
  VI. 2-chloro-4-isopropylamino-6-(γ-methoxy-propylamino)-s-triazine
  VII. 2-methoxy-4-ethylamino-6-sec-butylamino-s-triazine
  VIII. "Cotofor" (2-ethylthio-4,6-bis(isopropylamino)-s-triazine
  IX. Monuron Antidotes: according to the active ingredients of the formula I numbered in the table Test plants: summer wheat and summer barley.

| Results in summer wheat (Colibri variety) | | | | |
|---|---|---|---|---|
| (a) Herbicide (H) | Antidote (A) | Herbicide alone 2 kg/ha | H + A 2+2 kg/ha | 2+1 kg/ha |
| I | 27 | 6 | 8 | 9 |
| II | 33 | 3 | 6 | 7 |
| III | 54 | 1 | 4 | 4 |
| IX | 15 | 2 | 5 | 5 |
| (b) Herbicide | Antidote | Herbicide alone 1 kg/ha | H + A 1+1 kg/ha | 1+0.5 kg/ha |
| IV | 48 | 2 | 8 | 8 |
| V | 41 | 3 | 6 | 6 |
| VI | 40 | 4 | 7 | 6 |
| III | 54 | 2 | 6 | 7 |
| VII | 55 | 2 | 6 | 6 |

| (a) Herbicide (H) | Antidote (A) | Herbicide alone 2 kg/ha | H + A 2 + 2 kg/ha | 2 + 1 kg/ha |
|---|---|---|---|---|
| VIII | 35 | 4 | 9 | 9 |
| IX | 15 | 2 | 7 | 6 |
| IX | 42 | 2 | 8 | 9 |

| (b) Herbicide (H) | Antidote (A) | Herbicide alone 1 kg/ha | H + A 1 + 1 kg/ha | 1 + 0.5 kg/ha |
|---|---|---|---|---|
| IV | 48 | 4 | 7 | 7 |
| V | 20 | 3 | 7 | 6 |
| V | 40 | 3 | 7 | 6 |
| V | 54 | 1 | 7 | 7 |
| V | 55 | 1 | 7 | 6 |
| VI | 48 | 3 | 6 | 7 |
| III | 48 | 7 | 9 | 9 |
| III | 54 | 7 | 9 | 9 |

Test 4

Test of the safening effect of a number of antidotes on the herbicide 2-chloro-4-ethylamino-6-tert-butylamino-s-triazine in summer wheat ("Colibri" variety) and summer barley ("Mazurka" variety).

Concentrations:
  herbicide: 1 kg/ha alone
  Herbicide + antidote: 1 + 1/1 + 1.05/1 + 0.25 kg/ha

| herbicide: kg/ha → antidote: kg/ha → No. | 1 | | | | 1 | | | |
|---|---|---|---|---|---|---|---|---|
| | 0 | 1 | 0.5 | 0.25 | 0 | 1 | 0.5 | 0.25 |
| 84 | 3 | 7 | 6 | 4 | 5 | 9 | 7 | 6 |
| 85 | 3 | 6 | 4 | 4 | 5 | 9 | 9 | 9 |
| 86 | 3 | 6 | 6 | 4 | 5 | 9 | 7 | 6 |
| 87 | 3 | | 7 | 7 | 5 | 7 | 9 | 9 |
| 89 | | | | | 5 | 9 | 9 | 9 |
| 90 | | | | | 5 | 9 | 9 | 3 |
| 92 | | | | | 5 | 9 | 7 | 9 |
| 93 | 3 | 9 | 9 | 6 | 5 | 9 | 9 | 9 |
| 3 | 3 | 7 | 7 | 4 | 5 | 7 | 6 | 9 |
| 94 | 3 | 7 | 7 | 7 | 5 | 9 | 9 | 9 |
| 95 | 3 | 7 | 5 | 6 | 5 | 7 | 7 | 6 |
| 96 | 3 | 7 | 7 | 5 | 5 | 9 | 7 | 6 |
| 97 | | | | | 5 | 7 | 9 | 9 |
| 98 | 3 | 6 | 6 | | 5 | 9 | 9 | 8 |
| 99 | 3 | 6 | 6 | 6 | | | | |
| 100 | 3 | 7 | 7 | 5 | 5 | 9 | 9 | 9 |
| 4 | 3 | 9 | 9 | 6 | | | | |
| 5 | 3 | 7 | 7 | 8 | | | | |
| 101 | 3 | 9 | 9 | 5 | | | | |
| 102 | 3 | 9 | 9 | | | | | |
| 103 | 3 | 7 | | | | | | |
| 6 | 3 | 5 | 9 | 9 | | | | |
| 7 | 3 | 9 | 9 | 9 | | | | |
| 104 | 3 | 7 | 7 | 9 | | | | |
| 105 | 3 | 7 | 7 | 8 | | | | |
| 8 | 3 | 9 | 9 | | | | | |

At a concentration of 1 kg/ha without antidote, the tested herbicide achieved the average damage rating of 3 in summer wheat, whereas it damages summer barley less severely (rating 5). Under certain test conditions the damage is still less, e.g. rating 6 in wheat and rating 7 in barley. In these cases, the comparison values with antidote were omitted from the table, as the improvements there no longer permit any practical numerical evaluation.

The composition of the invention containing the novel active ingredient combination additionally contains suitable carriers and/or other adjuvants. Suitable carriers and adjuvants can be solid or liquid and correspond to the substances ordinarily employed in the art of formulation, for example natural or regenerated mineral substances, solvents, dispersants, wetting agents, tackifiers, thickeners, binders or also fertilisers.

The content of active ingredient in commercial compositions is between 0.1 and 95, preferably between 1 and 80, percent by weight.

For application, the active ingredient combination can be processed to the following liquid formulations (the percentages by weight in brackets denote advantageous amounts of active substance):

Solid formulations: dusts, tracking agents, (up to 10%) granules (coated granules, impregnated granules and homogeneous granules) (1 to 80%);

Liquid formulations:
(a) active substance concentrates which are dispersible in water; wettable powders and pastes (25–90% in commercial packs, 0.01 to 15% in ready for use solution); emulsifiable concentrates and concentrated solutions (10 to 50%; 0.01 to 15% in ready for use solution);
(b) solutions (0.01 to 20%).

Solid forms (dusts, tracking powders, granules), are obtained by mixing the active ingredients with solid carriers. Suitable carriers are, for example: kaolin, talc, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulfates, magnesium oxide, ground synthetic materials, fertilisers, for example ammonium sulfate, ammonium phosphate, ammonium nitrate, urea, ground vegetable products, such as corn meal, bark dust, sawdust, nutshell meal, cellulose powder residues of plant extractions, activated charcoal etc. These substances can either be used singly or in admixture with one another.

Granulates can be prepared by dissolving the active ingredients in an organic solvent and applying the resultant solution to a granulated material, for example attapulgite, $SiO_2$, granicalcium, bentonite etc., and then evaporating the solvent.

Polymer granulates can also be prepared by impregnating a finished, porous polymer granulate (urea/formaldehyde polymers, polyacrylonitrile, polyester and others), which has a specific surface area and a favourable predetermined adsorption/desorption ratio, with the active ingredients, for example in the form of their solutions (in a low boiling solvent) and removing the solvent. Polymer granulates of this kind in the form of microgranules having a bulk density of 300 g/liter to 600 g/liter can also be produced with the aid of atomisers. The dusting can be carried out from aircraft over extensive treatment areas.

It is also possible to obtain granulates by compacting the carrier with the active ingredients and adjuvants and subsequently comminuting the product.

To these mixtures can also be added additives which stabilize the active ingredients and/or nonionics, anionics and cationics, which, for example, improve the adhesion of the active ingredients on plants or parts of plants (adhesives and sticking agents) and/or ensure a better wettability (wetting agents) and dispersibility (dispersing agents). Examples of suitable adhesive substances are: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl moiety, ligninsulfonic acids, the alkali metal and alkaline earth metal salts thereof, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of urea and formaldehyde, and also latex products.

Water-dispersible concentrates, i.e. wettable powders, pastes and emulsifiable concentrates, are compositions which can be diluted with water to the desired concentration. They consist of active ingredient, carrier, optionally additives which stabilize the active ingredient, surface-active substances and anti-foam agents and, if appropriate, solvents.

Wettable powders and pastes are obtained by mixing and grinding the active ingredients with dispersing agents and pulverulent carriers in suitable devices until homogeneity is attained. Suitable carriers are, for example, those already mentioned for the solid formulations. In some cases it is advantageous to use mixtures of different carriers. As dispersing agents there can be used, for example, condensation products of sulfonated naphthalene and sulfonated naphthalene derivatives with formaldehyde, condensation products of naphthalene or naphthalenesulfonic acids with phenol and formaldehyde, as well as alkali metal, ammonium and alkaline earth metal salts of ligninsulfonic acid, in addition, alkylarylsulfonates, alkali metal and alkaline earth metal salts of dibutylnaphthalenesulfonic acid, fatty alcohol sulfates, such as salts of sulfated hexadecanols, heptadecanols, octadecanols, and salts of sulfated fatty alcohol glycol ethers, the sodium salt of oleyl methyl tauride, ditertiary ethylene glycols, dialkyldilaurylammonium chlorides and fatty acid alkali metal and alkaline earth metal salts.

Suitable anti-foams are silicones.

The active ingredients are mixed, ground sieved and strained with the additives mentioned above such that, in wettable powders, a solid particle size of 0.02 to 0.04 mm and in pastes, of 0.03 mm, is usually not exceeded. Emulsifiable concentrates and pastes are formulated by using dispersing agents, such as those cited previously above, organic solvents, and water. Examples of suitable solvents are: alcohols, xylenes, toluene, dimethyl sulfoxide, N,N-dialkylated amides and trialkylamines. The solvents must be practically odourless, not phytotoxic, inert to the active substances, and not readily combustible.

Furthermore, the compositions of the invention can be applied in the form of solutions. To this end, both active substances (a) and (b) are dissolved in suitable organic solvents, mixtures of solvents, water, or mixtures of organic solvents and water. Aliphatic and aromatic hydrocarbons, chlorinated derivatives thereof or alkylnaphthalenes can be used as organic solvents.

The compositions of the present invention can be mixed with other biocidal active substances or compositions, e.g. insecticides, acaricides, fungicides, bactericides, growth regulators, rodenticides or nematocides, in order to broaden the activity spectrum.

The compositions of the invention can additionally contain plant fertilisers, trace elements and other substances which promote plant cultivation. It will be readily understood that compositions are also possible which contain several representatives of component (a) and/or component (b).

The following Examples will serve to illustrate in more detail the preparation of solid and liquid formulations containing the compounds of the invention. Throughout, parts and percentages are by weight.

Dust:

The following substances are used to formulate a 3% dust:
    3 parts of active ingredient mixture (1:1)
    97 parts of talc;

The active ingredients are mixed and ground with the carriers.

Granules:

The following substances are used to formulate 5% granules:
    5.00 parts of active ingredient mixture (a:b=2:1)
    0.25 parts of epichlorohydrin
    0.25 parts of cetyl polyglycol ether
    3.50 parts of polyethylene glycol
    91.00 parts of kaolin (particle size 0.3–0.8 mm).

The active ingredients are mixed with epichlorohydrin and the mixture is dissolved in 6 parts of acetone; the polyethylene glycol and cetyl polyglycol ether are then added. The resultant solution is sprayed on kaolin, and the acetone is subsequently evaporated in vacuo, Wettable powders:

The following constituents are used to formulate (a) a 70% and (b) a 25% wettable powder:

(a)

42 parts of 2-chloro-4-ethylamino-6-tert-butylamino-s-triazine
28 parts of active ingredient No. 53
5 parts of sodium dibutylnaphthalenesulfate
3 parts of naphthalenesulfonic acid/phenolsulfonic acid/formaldehyde condensate (3:2:1)
10 parts of kaolin
12 parts of Champagne chalk;

(b)

15 parts of Atrazine
10 parts of 4-(2'-cyano-4'-chlorophenoxy)-α-phenoxy-propionic acid isobutyl ester
5 parts of sodium oleylmethyltauride
2.5 parts of naphthalenesulfonic acid/formaldehyde condensate
0.5 parts of carboxymethyl cellulose
5 parts of neutral potassium aluminum silicate
62 parts of kaolin.

The active ingredients and adjuvants are applied to kaolin and chalk and then mixed and ground, to produce wettable powders of excellent wettability and suspension power. By diluting these wettable powders with water it is possible to obtain suspensions of the desired concentration. These suspensions can be used for the control of weeds and troublesome grasses in cereal crops.

Paste:

The following substances are used to formulate a 45% paste:
30 parts of a herbicidal triazine
15 parts of an antidote of the formula I
5 parts of sodium aluminium silicate
14 parts of cetyl polyethylene glycol ether with 8 moles of ethylene oxide
1 part of oleyl polyethylene glycol ether with 5 moles of ethylene oxide
2 parts of spindle oil
10 parts of polyethylene glycol.

The active ingredients are homogenised with the adjuvants is appropriate devices and ground. By diluting the resulting paste with water, it is possible to prepare suspensions of any desired concentration.

Emulsifiable concentrate:

The following ingredients are mixed to formulate a 25% emulsion concentrate:
25 parts of an active ingredient mixture (a:b=1:1)
5 parts of a mixture of nonylphenolpolyoxyethylene and calcium dodecylbenzenesulfonate
35 parts of 3,5,5-trimethyl-2-cyclohexen-1-one
35 parts of dimethyl formamide.

This concentrate can be diluted with water to give emulsions of suitable concentrations.

The active substance combination can be employed in one of the conventional formulations in the customary manner, for example by dusting, spraying, drenching, pouring of scattering.

What is claimed is:

1. A composition for the selective control of weeds in crops of wheat and barley which, in addition to containing conventional carriers and/or adjuvants, contains, as active herbicidal component a herbicidally effective amount of a 4,6-di-($C_1$–$C_4$ alkylamino)-s-triazine which is substituted in the 2-position by chlorine, bromine, methoxy, methylthio or ethylthio, and, as safening component a safening amount of a pyridyl ether derivative of the formula

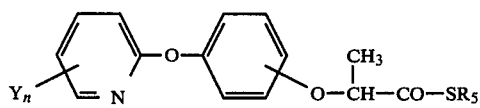

wherein
Y represents chlorine or trifluoromethyl;
n is an integer from 0 to 2; and
$R_5$ represents hydrogen, $C_1$–$C_4$ alkyl which is unsubstituted or substituted by chlorine or bromine, by $C_1$–$C_4$ alkyl, by the group

in which $R_a$ and $R_b$ are $C_1$–$C_4$ alkyl, or by cyano; $C_3$ or $C_4$ alkenyl, which is unsubstituted or monosubstituted by chlorine or bromine; $C_3$ or $C_4$ alkynyl which is unsubstituted or mono-substituted by chlorine or bromine; or phenyl;
in which the ratio of the herbicidal component to the safening component is in the range between 4:1 and 1:4.

2. A composition according to claim 1, wherein the active herbicidal component is 2-chloro-4-ethylamino-6-tert-butylamino-s-triazine.

3. A composition according to claim 2, wherein the safening component is the β-diethylaminoethyl ester of 4-(3',5'-dichloropyridyl-2'-oxy)-α-phenoxy-thiopropionic acid.

4. A composition according to claim 2, wherein the safening component is the propargyl ester of 4-(3',5'-dichloropyridyl-2'-oxy)-α-phenoxy-thiopropionic acid.

5. A pre-emergence method of selectively controlling weeds in crops of wheat and barley, which comprises treating sown wheat or barley crops or areas of land intended for cultivating wheat or barley, simultaneously or in succession, with a herbicidally effective amount of a herbicidal 4,6-di-($C_1$–$C_4$ alkylamino)-s-triazine which is substituted in the 2- position by chlorine, bromine, methoxy, methylthio or ethylthio, and a safening effective amount of a pyridyl ether derivative of the formula

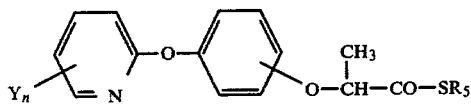

wherein
Y represents chlorine or trifluoromethyl;
n is an integer from 0 to 2; and
$R_5$ represents hydrogen; $C_1$–$C_4$ alkyl, which is unsubstituted or substituted by chlorine or bromine, by $C_1$–$C_4$ alkyl, by the group

in which $R_a$ and $R_b$ are $C_1$–$C_4$ alkyl, or by cyano; $C_3$ or $C_4$ alkenyl, which is unsubstituted or monosubstituted by chlorine or bromine; $C_3$ or $C_4$ alkynyl, which is unsubstituted or mono-substituted by chlorine or bromine; or phenyl;
in which the ratio of the 4,6-di-($C_1$–$C_4$ alkylamino)-s-triazine to the pyridyl ether derivative is in the range between 4:1 and 1:4.

* * * * *